United States Patent
Sobral et al.

(10) Patent No.: US 9,670,246 B2
(45) Date of Patent: Jun. 6, 2017

(54) PROCESS FOR THE ESTERIFICATION OF A CARBOTHIOIC ACID

(75) Inventors: Luis Sobral, Loures (PT); Dionisio Martin, Salamanca (ES); William Heggie, Palmela (PT); Emilia Leitão, São Marcos (PT)

(73) Assignee: Hovione Inter Ltd., Lucerne (CH)

( * ) Notice: Subject to any disclaimer, the term of this patent is extended or adjusted under 35 U.S.C. 154(b) by 1503 days.

(21) Appl. No.: 11/577,462

(22) PCT Filed: Dec. 2, 2004

(86) PCT No.: PCT/GB2004/005052
§ 371 (c)(1),
(2), (4) Date: Jul. 31, 2007

(87) PCT Pub. No.: WO2006/043015
PCT Pub. Date: Apr. 27, 2006

(65) Prior Publication Data
US 2007/0287846 A1    Dec. 13, 2007

(30) Foreign Application Priority Data

Oct. 19, 2004  (PT) .......................................... 103202

(51) Int. Cl.
C07J 3/00     (2006.01)
C07J 31/00    (2006.01)
(52) U.S. Cl.
CPC .................................. C07J 31/006 (2013.01)
(58) Field of Classification Search
USPC ....................................................... 552/610
See application file for complete search history.

(56) References Cited

U.S. PATENT DOCUMENTS

| | | | |
|---|---|---|---|
| 4,335,121 A | 6/1982 | Phillipps et al. | |
| 4,578,221 A | 3/1986 | Phillipps et al. | |

FOREIGN PATENT DOCUMENTS

| | | |
|---|---|---|
| GB | 2 088 877 A | 6/1982 |
| GB | 2 137 206 A | 10/1984 |
| WO | WO 97/24365 | 7/1997 |
| WO | WO 01/62722 A2 | 8/2001 |
| WO | WO 03/066654 A1 | 8/2003 |

OTHER PUBLICATIONS

Phillipps, Gordon H., et al., "Synthesis and Structure-Activity Relationships in a Series of Antiinflammatory Corticosteroid Analogues, Halomethyl Androstane-17β-carbothioates and-17β-carboselenoates," J. Med. Chem., 1994, pp. 3717-3729, vol. 37, American Chemical Society.

Foreign communication from a related counterpart application— International Search Report, PCT/GB2004/005052, Oct. 6, 2005, 4 pgs.
Foreign communication from a related counterpart application— International Preliminary Report on Patentability, PCT/GB2004/005052, Oct. 23, 2006, 8 pgs.
Kertesz, Denis J., et al., "Thiol Esters from Steroid 17B-Carboxylic Acids: Carboxylate Activation and Internal Participation by 17a-Acylates," J. Org. Chem., 1986, vol. 51, pp. 2315-2328, American Chemical Society.
Whitham, Gordon H., "Organosulfur Chemistry," 1995,Cover, Publishing Info and p. 3, (3 pages), Oxford University Press, USA.

*Primary Examiner* — Barbara P Badio
(74) *Attorney, Agent, or Firm* — Conley Rose, P.C.; Rodney B. Carroll

(57) ABSTRACT

A process for preparing compounds of formula [II]

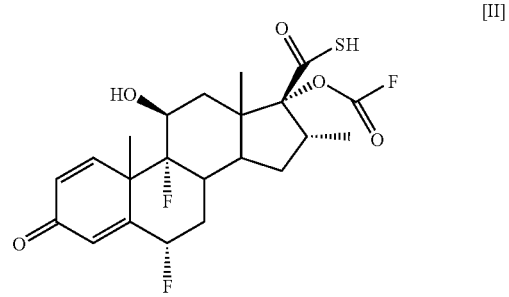

by esterification of the C-17 hydroxyl group of 6α,9α-difluoro-11β,17α-dihydroxy-16α-methyl-3-oxoandrosta-1,4-diene-17β-carbothioic acid, the compound of formula [I] comprises treating compound [I] with a slight excess of an acyl chloride of general formula R—COCl, where R represents —CH2CH3, —CH2CH2CH3 or —CH(CH3)2, in an inert solvent, in the presence of a tertiary amine.

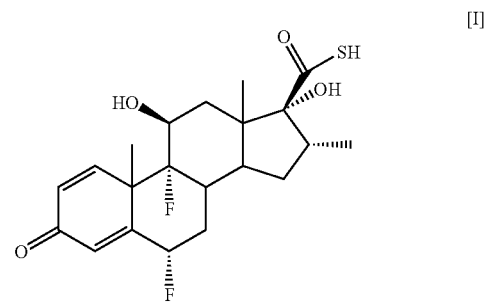

Preferably the process is carried out using pyridine in the presence of acetone at a temperature of from 5° C. to −20° C.

12 Claims, No Drawings

PROCESS FOR THE ESTERIFICATION OF A CARBOTHIOIC ACID

CROSS-REFERENCE TO RELATED APPLICATIONS

This application is a filing under 35 U.S.C. 371 of International Application No. PCT/GB2004/005052 filed Dec. 2, 2004, entitled "Process for the Esterification of a Carbothioic Acid," claiming priority of Portuguese Patent Application No. 103,202 filed Oct. 19, 2004, which applications are incorporated by reference herein in their entirety.

FIELD OF THE INVENTION

The present invention relates generally to a process for the esterification of a carbothioic acid, particularly but not exclusively in the preparation of fluticasone propionate; and to the use of certain intermediates.

In one aspect, the present invention relates to an improved process for the esterification of the C-17 hydroxyl group of 6α,9α-difluoro-11β,17α-dihydroxy-16α-methyl-3-oxoandrosta-1,4-diene-17β-carbothioic acid, compound of formula [I], comprising treating this intermediate with a slight excess of an acyl chloride of general formula R—COCl, where R represents, —CH$_2$CH$_3$, —CH$_2$CH$_2$CH$_3$ or —CH(CH$_3$)$_2$, in the presence of an appropriate tertiary amine, in an inert solvent, at a temperature between 5° C. and −20° C., to obtain selectively the 17α-acyl derivative of formula [II].

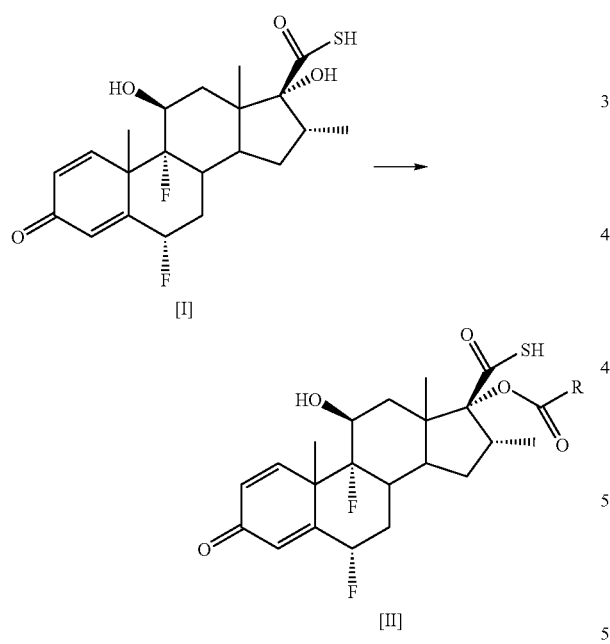

This invention provides an esterification process which is simpler and more economically efficient than those disclosed in the prior art because it suppresses one of the two chemical reactions described in those processes. Another feature of the process of this invention is that it yields 17α-esters of high purity.

More particularly, this invention relates to an improved process for the preparation of 6α,9α-difluoro-11β-hydroxy-16α-methyl-17α-propionyloxy-3-oxoandrosta-1,4-diene-17β-carbothioic acid, compound of formula [III] which is an intermediate in the synthesis of fluticasone propionate, an active ingredient used as an anti-inflammatory steroid, effective for the treatment of inflammatory diseases such as asthma and chronic obstructive pulmonary disease.

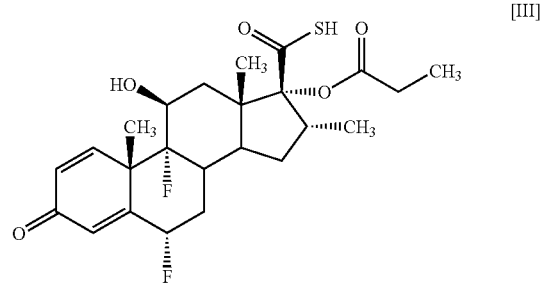

BACKGROUND OF THE INVENTION

U.S. Pat. No. 4,335,121, British patents GB 2,088,877, GB 2,137,206, U.S. Pat. No. 4,578,221 and J. Med. Chem., 1994, 37, 3717-3729, describe the 17α-propionylation of compound [I], to obtain the fluticasone propionate intermediate [III], through the two chemical steps illustrated below, via the mixed anhydride compound [IV].

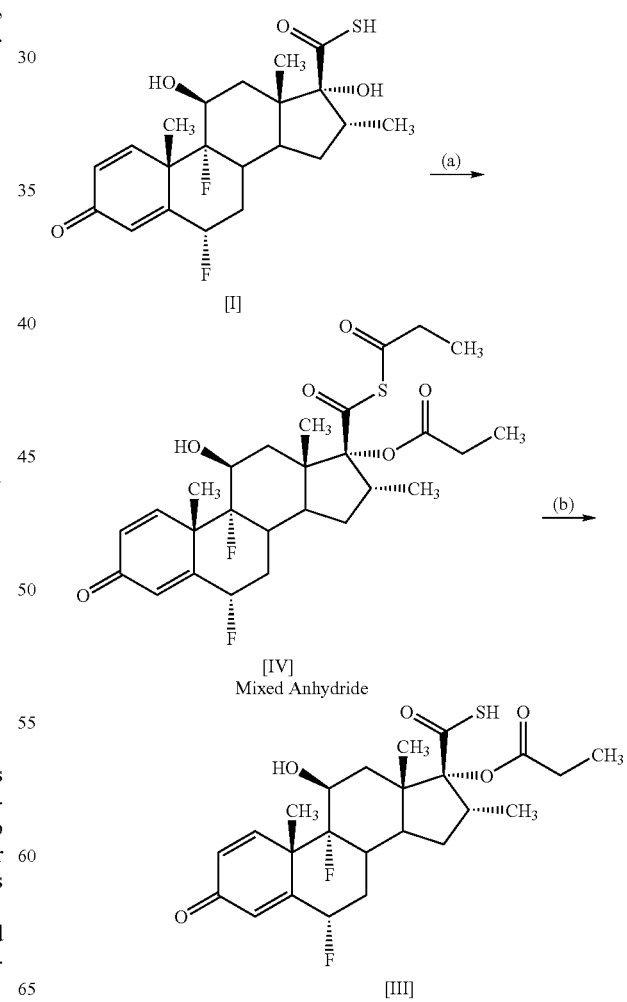

In the first step (a), the mixed anhydride [IV] is prepared with an excess of at least 2 moles of propionyl chloride per mol of compound [I], in the presence of triethylamine and using dichloromethane as solvent. Upon conclusion of the propionylation reaction, the reaction mixture is worked-up and a buff solid is obtained. In the second step (b), this solid is dissolved in acetone and treated with diethylamine, to convert the mixed anhydride to compound [III]. Once the aminolysis reaction is complete, the reaction mixture is worked up to isolate compound [III].

International patent application WO 03/066654 claims the preparation of intermediate [III] by: (a) reacting compound [I] with at least 1.3 moles of an activated derivative of propionic acid per mol of compound [I], and removal of the sulphur linked moiety from any compound of formula [IV] with an organic primary or secondary amine such as diethanolamine or N-methylpiperazine.

Patent application WO 01/62722 discloses the 17α-esterification of the hydroxyacid compound [V] with an alkanoyl halide, in presence of a base, and particularly describes the preparation of the 17α-propionate compound of formula [VI]

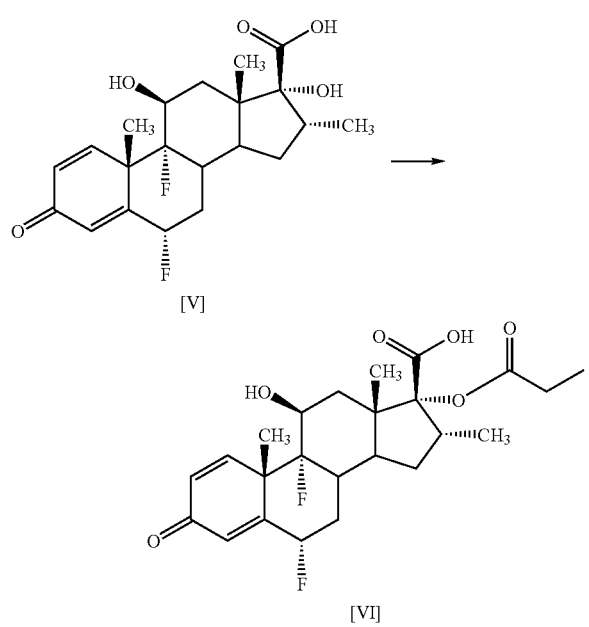

by: (a) reacting the hydroxyacid of formula [V] with 2.3 moles of propionyl chloride per mol of compound [V], using triethylamine as base, and (b) in situ reacting the compound obtained in (a) with diethylamine.

All of the 17α-acylation procedures described in the prior art, either for the carbothioic acid [I] or the related carboxylic acid [V], use an excess of the acylating agent to ensure completion of the 17α-acylation, thus requiring aminolysis, with an adequate primary or secondary amine, of any mixed anhydride formed.

SUMMARY OF THE INVENTION

We have now found that the transformation of the carbothioic acid compound [I] into the compounds of general formula [II], can selectively take place directly, with negligible formation of the correspondent mixed anhydride, under conditions herein described below. By following the process of the present invention, the intermediate 6α,9α-difluoro-11β,17α-dihydroxy-16α-methyl-3-oxoandrosta-1,4-diene-17β-carbothioic acid, compound [I], is directly converted to compounds of general formula [II]

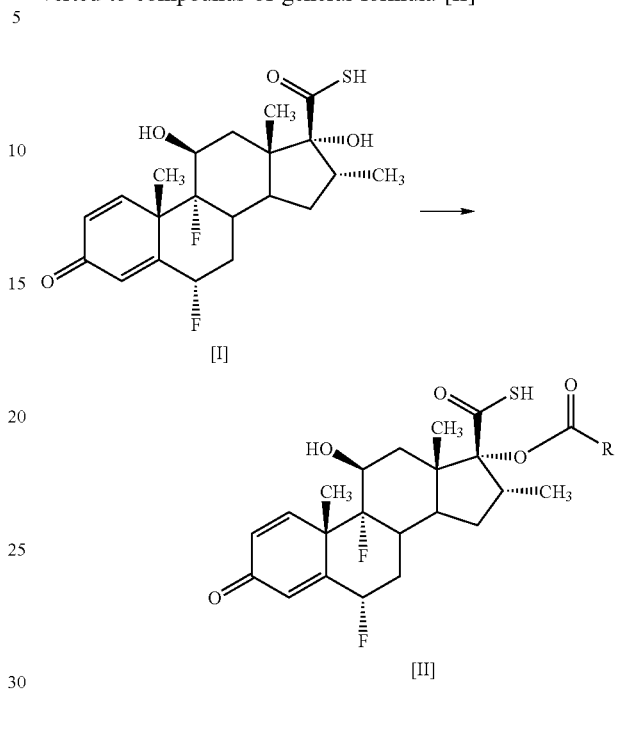

by reaction with a slight excess of the corresponding acyl chloride, in an inert solvent, in the presence of an appropriate tertiary amine.

The particular advantage of the present invention over those of the prior art is that compounds of general formula [II] are obtained directly from compound [I], without the need to perform the aminolysis of the corresponding mixed anhydride. Additionally, under the aminolysis conditions described in the prior art, the chemical stability of carbothioic acid derivatives such as compound [III] is limited therefore, the simplified process of this invention, by eliminating the aminolysis reaction, affords 17α-esters of higher purity.

DETAILED DESCRIPTION OF THE INVENTION

According to the present invention, there is provided a process for preparing compounds of formula [II]

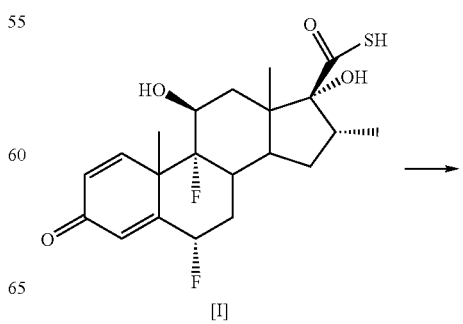

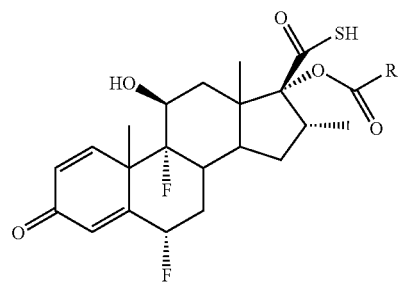

[II]

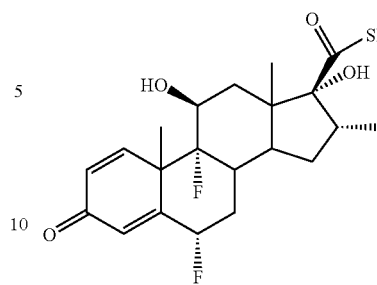

[I]

by esterification of the C-17 hydroxyl group of 6α,9α-difluoro-11β,17α-dihydroxy-16α-methyl-3-oxoandrosta-1,4-diene-17β-carbothioic acid, compound of formula [I], which process comprises treating compound [I] with a slight excess of an acyl chloride of general formula R—COCl, where R represents —CH$_2$CH$_3$, —CH$_2$CH$_2$CH$_3$ or —CH(CH$_3$)$_2$, in an inert solvent, in the presence of a tertiary amine. Preferably, the process is carried out at a temperature of from 5° C. to −20° C.

The invention also provides the use of compounds of formula [II] when made according to the process of the invention for the preparation of therapeutically useful medicaments.

The present invention provides an improved and simplified process for the selective 17α-esterification of the compound [I], forming negligible amounts of mixed anhydrides of general formula [VII]

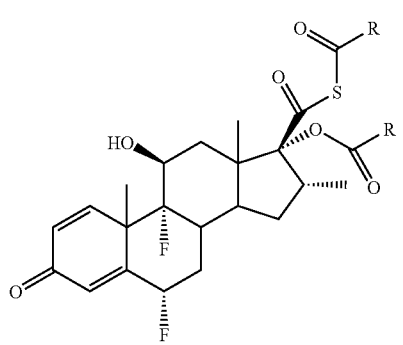

[VII]

in which R represents —CH$_2$CH$_3$, —CH$_2$CH$_2$CH$_3$ or —CH(CH$_3$)$_2$, without the need to perform the aminolysis reaction of the corresponding mixed anhydrides.

The process comprises the reaction of compound [I], 6α,9α-difluoro-11β,17α-dihydroxy-16α-methyl-3-oxoandrosta-1,4-diene-17β-carbothioic acid, with a slight excess of an acyl chloride of general formula R—COCl, in which R represents —CH$_2$CH$_3$, —CH$_2$CH$_2$CH$_3$ or —CH(CH$_3$)$_2$, in the presence of an appropriate organic tertiary amine, in an inert solvent, to yield the compounds of general formula [II]

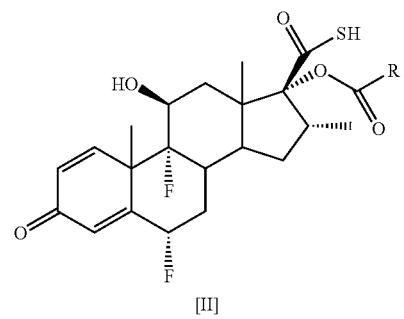

[II]

in which R represents —CH$_2$CH$_3$, —CH$_2$CH$_2$CH$_3$ or —CH(CH$_3$)$_2$.

A particularly preferred embodiment of the present invention is to provide an improved process for the preparation of 6α,9α-difluoro-11β-hydroxy-16α-methyl-17α-propionyloxy-3-oxoandrosta-1,4-diene-17β-carbothioic acid, compound of formula [III], comprising of reacting 6α,9α-difluoro-11β,17α-dihydroxy-16α-methyl-3-oxoandrosta-1,4-diene-17β-carbothioic acid [II] with a slight excess of propionyl chloride, in the presence of an appropriate tertiary amine, in an inert solvent.

The compound of formula [III] is a known intermediate useful in the preparation of anti-inflamatory steroids such as fluticasone propionate of formula [A] (described in U.S. Pat. No. 4,335,121), highly effective in the treatment of inflammatory diseases like asthma and chronic obstructive pulmonary disease (COPD), and in the preparation of the related 6α,9α-difluoro-11β-hydroxy-16α-methyl-3-oxo-17α-propionyloxy-androsta-1,4-diene-17β-carbothioic acid S-(2-oxo-tetrahydro-furan-3-yl) ester of formula [B] (described in the application WO 97/24365), possessing a useful anti-inflammatory activity and having little or no systemic activity.

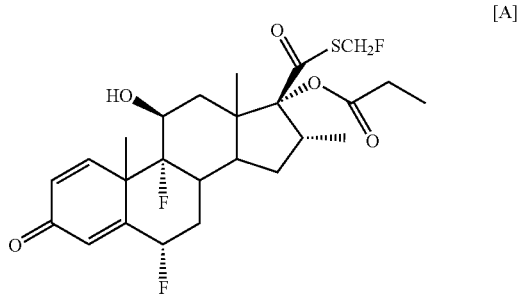

[A]

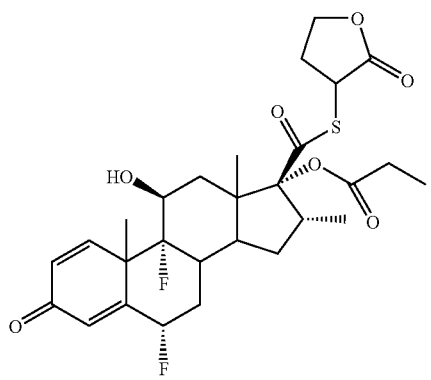

[B]

Accordingly, the invention also provides a process for preparing fluticasone propionate which process comprises preparing 6α,9α-difluoro-11β-hydroxy-16α-methyl-17α-propionyloxy-3-oxoandrosta-1,4-diene-17β-carbothioic acid according to the process of the invention and converting the said compound to fluticasone propionate.

There is also provided a process for the preparation of 6α-9α-difluoro-11β-hydroxy-16α-methyl-3-oxo-17α-propionyloxy-androsta-1,4-diene-17β-carbothioic acid S-(2-oxo-tetrahydrofuran-3-yl) ester which process comprises preparing 6α, 9α-difluoro-11β-hydroxy-16α-methyl-17α-propionyloxy-3-oxoandrosta-1,4-diene-17β-carbothioic acid according to the process of the invention and converting said compound to the said S-ester.

The present invention provides an advantageous process for the preparation of 6α,9α-difluoro-11β-hydroxy-16α-methyl-17α-propionyloxy-3-oxoandrosta-1,4-diene-17β-carbothioic acid, compound of formula [III] comprising of treating the compound [I], 6α,9α-difluoro-11β,17α-dihydroxy-16α-methyl-3-oxoandrosta-1,4-diene-17β-carbothioic acid, with a slight excess of propionyl chloride, in the presence of an appropriate tertiary amine, in an inert solvent, at a temperature between 5° C. and −20° C.

The acyl chloride of general formula R—COCl is preferably used in the process of the present invention in a molar ratio of from 1.0 to 1.2 moles of acyl chloride per mol of starting compound [I], preferably in an amount within this range.

Inert solvents for the 17α-acylation process of the present invention include acetone, tetrahydrofuran, dimethylacetamide, dichloromethane, ethyl acetate, 2-pentanone, 3-pentanone, 4-methyl-2-pentanone and 2-butanone. Acetone is the preferred solvent.

Appropriate tertiary amines to carry out the selective 17α-propionylation include pyridine, 2-picoline 3-picoline, 4-picoline, N-methylimidazole, and N-methylpyrrolidine.

The 17α-acylation reaction of the invention is preferably performed at a temperature of from 5° C. to −20° C.

The use of the tertiary amines defined above as adequate for the process of the patent, present advantages over other bases previously described in the prior art such as triethylamine, tripropylamine, ethyldiisopropylamine, N,N-dimethylaniline, N,N-dimethylcyclohexylamine, inorganic carbonates such as e.g. sodium hydrogen carbonate, potassium carbonate and sodium carbonate. When using these bases the formation of high levels of the mixed anhydride compound [IV] or incomplete consumption of compound [I] or the formation of high levels of impurities is as is the case when sodium hydrogen carbonate is avoided.

Under the preferred conditions of the process of the present invention, 17α-esterification goes to completion with 1.0 to 1.2 moles of propionyl chloride per mole of compound [I], in the presence of pyridine, and the levels of mixed anhydride formed during the reaction are below 3% (in area, by HPLC). With these low levels of mixed anhydride, the aminolysis reaction is not required and compound [III] is isolated with a high degree of purity, on work-up of the propionylation reaction.

Under the conditions described in the prior art when compound [III] is prepared via the mixed anhydride, partial degradation of compound [III] may occur during the aminolysis reaction. This degradation is especially problematic when prolonged reaction times take place, which is to be expected on an industrial scale. Under the conditions disclosed in the present invention, this in situ degradation of compound [III] is avoided.

We have found that by following the prior art a precursor (G precursor) to an impurity (impurity G) is formed.

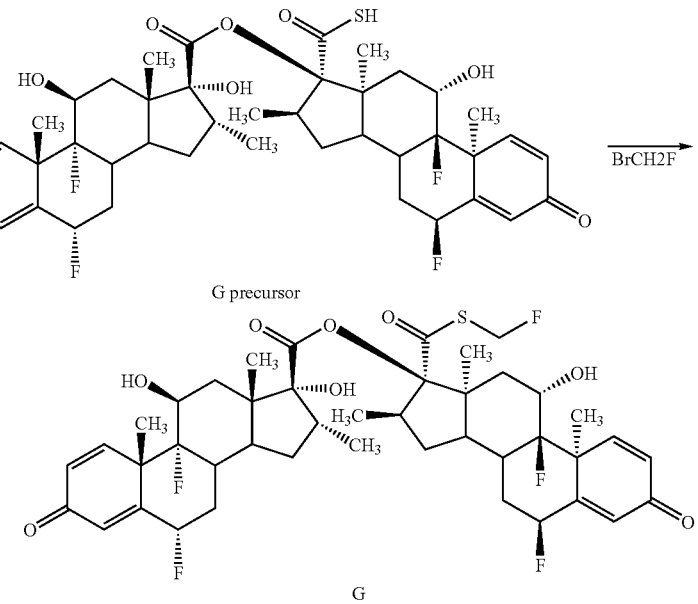

G precursor

G

With the process of the present invention, dimer G, which is difficult to remove from the final product, fluticasone propionate, by recrystallization when at levels higher than 0.5%, is formed at levels below 0.3%. Hence, repeated recrystallizations to obtain material of the required purity, which if carried out significantly reduces the overall yield, are avoided.

Another embodiment of this invention is to provide an improved process for the preparation of the compounds 6α,9α-difluoro-11β-hydroxy-16α-methyl-17α-butyryloxy-3-oxoandrosta-1,4-diene-17β-carbothioic acid, compound of formula [VIII] and 6α,9α-difluoro-11β-hydroxy-16α-methyl-17α-isobutyryloxy-3-oxoandrosta-1,4-diene-17β-carbothioic acid of formula [IX].

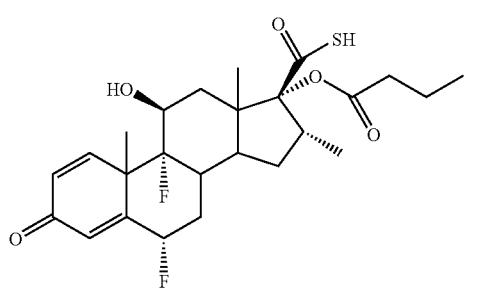

[VIII]

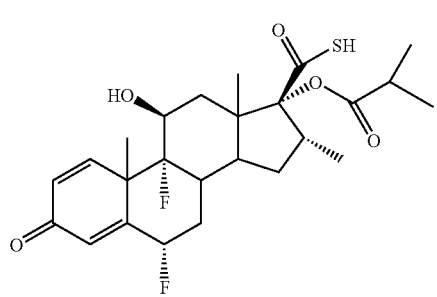

[IX]

Compounds of formula [VIII] and [IX] are directly prepared from compound [I] by reaction with a slight excess of the corresponding acyl chloride, without the need to perform an aminolysis reaction of the corresponding mixed anhydrides.

According to a preferred aspect of to the present invention, esterification of compound. [I] to obtain compound [VIII], is performed with 1.0 to 1.2 moles of butyryl chloride, in acetone, in the presence of pyridine, at a temperature between 5° C. and −20° C., preferably between 5° C. and 0° C. The esterification of compound [I] to obtain compound [IX] is preferably performed with 1.0 to 1.2 moles of isobutyryl chloride, in acetone, in the presence of pyridine, at a temperature between 5° C. and −20° C., preferably between 5° C. and 0° C.

EXAMPLES

The following examples illustrate the invention and certain preferred embodiments and are exempt of limitative character of the scope of the invention.

Example 1: Preparation of 6α,9α-difluoro-11β-hydroxy-16α-methyl-17α-propionyloxy-3-oxoandrosta-1,4-diene-17β-carbothioic acid A suspension of compound [I] (10 g, 0.024 moles) in acetone (175 ml) is cooled to −20° C. and treated with pyridine (30 ml) and propionyl chloride (2.3 ml, 0.026 moles), while maintaining the temperature between −20° C. and −15° C. The mixture is stirred at −20° C./−15° C. until completion of reaction. A second addition of propionyl chloride (0.02 ml) can be carried out if necessary to complete the reaction. Compound [III] is precipitated by addition of water (240 ml) and concentrated hydrochloric acid (30 ml). The suspension is stirred for 2 hours at a temperature between 0° C. and 5° C., filtered, and the wet cake washed with cold water until neutral pH. The solid is dried at a temperature below 40° C., under vacuum, to give the title compound as a white to off white solid (10.04 g; 88%; Purity, area % by HPLC: 96.1%).

Example 2: Preparation of 6α,9α-difluoro-11β-hydroxy-16α-methyl-17α-isobutyryloxy-3-oxoandrosta-1,4-diene-17β-carbothioic acid Isobutyryl chloride (0.28 ml, 0.0027 moles) is slowly added to a mixture of acetone (17.5 ml), compound [I] (1 g, 0.0024 moles) and pyridine (3 ml), at temperatures between 5° C. and 0° C., and the mixture is stirred at that temperature range until consumption of compound [I]. Upon completion of the reaction the title compound is precipitated by addition of water (24 ml) and concentrated hydrochloric acid (3 ml). The suspension is stirred for 1 to 2 hours, at a temperature between 0° C. and 5° C., filtered, and the wet cake washed with cold water until neutral pH. The wet solid is dried at a temperature lower than 40° C., under vacuum, to yield the title compound as a white to off white solid (1.09 g; 93%; Purity, area % by HPLC: 94.8%).

Example 3: Preparation of 6α,9α-difluoro-11β-hydroxy-16α-methyl-17α-propionyloxy-3-oxoandrosta-1,4-diene-17β-carbothioic acid A suspension of compound [I] (1 g, 0.0024 moles) in acetone (17 ml) is cooled to a temperature between −20° C. and −15° C. N-methylimidazole (2.9 ml) and propionyl chloride (0.23 ml, 0.0026 moles) are sequentially added to the solution, maintaining the temperature between −20° C. and −15° C. Upon completion of the reaction, compound [III] is precipitated by addition of water (24 ml) and concentrated hydrochloric acid (3 ml). The suspension is stirred for 2 hours at ca. 0° C., filtered, and the wet cake washed with cold water until neutral pH. The wet solid is dried at a temperature below 40° C., under vacuum, to give the title compound as a white to off white solid (1.0 g; 88%; Purity, area % by HPLC: 96.8%).

The invention claimed is:

1. A process for preparing fluticasone propionate comprising:
   (i) esterification of the C-17 hydroxyl group of 6α,9α-difluoro-11β,17α-dihydroxy-16α-methyl-3-oxoandrosta-1,4-diene-17β-carbothioic acid, the compound of formula [I]:

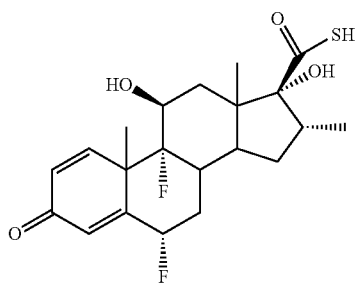

(ii) wherein esterification comprises contacting compound [I] with from 1.0 mol to 1.2 moles of an acyl chloride of general formula R—COCl per mol of compound [I], in an inert solvent, in the presence of a tertiary amine at a temperature of from 5° C. to 0° C., where R represents —CH$_2$CH$_3$, wherein the tertiary amine is pyridine, 2-picoline, 3-picoline, 4-picoline, N-methylimidazole, or N-methylpyrrolidine to produce compound [II], 6α,9α-difluoro-11β-hydroxy-16α-methyl-17α-propionyloxy-3-oxoandrosta-1,4-diene-17β-carbothioic acid:

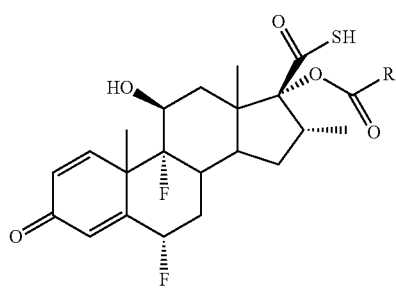

and (iii) converting compound [II] to fluticasone propionate wherein the fluticasone propionate contains less than 0.3% dimer G

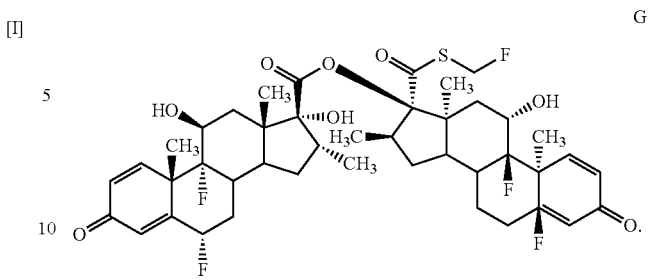

2. The process according to claim 1 wherein the acyl chloride of general formula R—COCl is propionyl chloride, R representing —CH$_2$CH$_3$.

3. The process according to claim 1 wherein the tertiary amine is pyridine, or N-methylimidazole.

4. The process according to claim 1 wherein the tertiary amine is pyridine.

5. The process according to claim 1 wherein the inert solvent is acetone.

6. The process according to claim 1 wherein pyridine is used as the tertiary amine and the inert solvent is acetone, tetrahydrofuran, dimethylacetamide, dichloromethane, ethyl acetate, 2-pentanone, 3-pentanone, 4-methyl-2-pentanone or 2-butanone.

7. A process for the preparation of 6α,9α-difluoro-11β-hydroxy-16α-methyl-3-oxo-17α-propionyloxy-androsta-1,4-diene-17β-carbothioic acid S-(2-oxo-tetrahydrofuran-3-yl)-ester which process comprises preparing 6α,9α-difluoro-11β-hydroxy-16α-methyl-3-oxo-17α-propionyloxy-3-oxoandrosta-1,4-diene-17β-carbothioic acid according to the process of claim 1, and converting said compound to the said S-ester.

8. The process according to claim 2 wherein the tertiary amine is pyridine, or N-methylimidazole.

9. The process according to claim 4 wherein the inert solvent is acetone.

10. The process according to claim 8 wherein the inert solvent is acetone.

11. The process according to claim 1 wherein the process does not comprise an aminolysis step.

12. The process according to claim 1 wherein the process does not comprise an aminolysis step with a primary or secondary amine.

* * * * *